United States Patent
Meyers (10) Patent No.: US 8,991,647 B2
(45) Date of Patent: Mar. 31, 2015

(54) COMBINATION TOILET PAPER DISPENSER, DISINFECTING STATION, AND DEODORIZING STATION

(75) Inventor: Leigh A. Meyers, Cleveland, TX (US)

(73) Assignee: Encore Industrial Supply, LLC, Houston, TX (US)

(*) Notice: Subject to any disclaimer, the term of this patent is extended or adjusted under 35 U.S.C. 154(b) by 212 days.

(21) Appl. No.: 13/431,212

(22) Filed: Mar. 27, 2012

(65) Prior Publication Data

US 2012/0248136 A1 Oct. 4, 2012

Related U.S. Application Data

(60) Provisional application No. 61/471,235, filed on Apr. 4, 2011.

(51) Int. Cl.
| | | |
|---|---|---|
| A47F 1/00 | (2006.01) | |
| A24F 25/00 | (2006.01) | |
| A61L 9/04 | (2006.01) | |
| B65H 16/02 | (2006.01) | |
| A47K 10/38 | (2006.01) | |
| A61L 9/12 | (2006.01) | |
| A61L 2/22 | (2006.01) | |
| A47K 10/32 | (2006.01) | |

(52) U.S. Cl.
CPC ....... *A47K 10/3836* (2013.01); *A47K 2010/322* (2013.01); *A47K 2010/324* (2013.01); *A47K 2010/326* (2013.01); *A47K 2010/3266* (2013.01); *A61L 9/122* (2013.01); *A61L 2/22* (2013.01); *A61L 9/048* (2013.01)
USPC ............. 221/96; 239/52; 239/289; 239/6; 422/5; 422/120; 422/123; 422/124; 242/564.1; 242/598.1; 242/599; 242/594; 261/30; 439/148

(58) Field of Classification Search
USPC .......... 422/5, 120, 123, 124; 221/96; 239/52, 239/289, 6; 261/30; 242/564.1, 598.1, 594, 242/599; 439/148
See application file for complete search history.

(56) References Cited

U.S. PATENT DOCUMENTS

| | | | |
|---|---|---|---|
| 3,192,008 A * | 6/1965 | Dwyer | 422/124 |
| 4,667,846 A | 5/1987 | Marceau | |
| 5,413,251 A * | 5/1995 | Adamson | 222/129 |
| 5,660,313 A | 8/1997 | Newbold | |
| 5,681,364 A * | 10/1997 | Fortune | 55/400 |
| 5,887,759 A | 3/1999 | Ayigbe | |
| 5,888,261 A * | 3/1999 | Fortune | 55/400 |
| 6,918,513 B1 | 7/2005 | Downey | |
| 6,969,024 B2 | 11/2005 | He et al. | |
| D521,289 S | 5/2006 | Breitinger | |
| D552,902 S | 10/2007 | Sadeh et al. | |
| 7,354,598 B2 * | 4/2008 | Masting | 424/443 |

(Continued)

*Primary Examiner* — Rakesh Kumar
(74) *Attorney, Agent, or Firm* — Adolph Locklar (57) ABSTRACT

A station combines a toilet paper dispenser, dispenser for dispensing hand wipes, a dispenser for dispensing surface antibiotic wipes, and a deodorant feature. The station includes a toilet paper dispenser made from a plastic type material and the toilet paper dispenser may be a single or double roll dispenser. The station cover houses a battery-operated fan that pulls air from inside the dispenser. A tray inside the dispenser holds a fragrance cup holding a quantity of deodorant. The base holds one or two rolls of commercial toilet paper, each of which rolls on a hollow plastic axle to hold a bottle containing wipes. A microswitch may be integrated in the cover to disengage the fan when the cover of the unit is open.

20 Claims, 5 Drawing Sheets

(56) References Cited

U.S. PATENT DOCUMENTS

| | | |
|---|---|---|
| 7,374,128 B2 | 5/2008 | Hendrix et al. |
| 7,461,758 B2 | 12/2008 | Serfaty |
| 7,578,388 B2 | 8/2009 | O'Connell et al. |
| 7,757,351 B2 | 7/2010 | Davis, Jr. |
| 7,856,941 B2 | 12/2010 | Nelson et al. |
| D632,511 S | 2/2011 | Sallack |
| 8,444,007 B2 * | 5/2013 | Hatter et al. ............ 221/45 |
| 8,479,957 B2 * | 7/2013 | Ophardt ............ 222/192 |
| 8,747,755 B2 * | 6/2014 | Larsson ............ 422/123 |
| 8,763,948 B1 * | 7/2014 | Holowaty ............ 242/564.4 |
| 2001/0006206 A1 * | 7/2001 | Helfer-Grand ............ 242/564.1 |
| 2004/0124101 A1 * | 7/2004 | Mitchell et al. ............ 206/205 |
| 2004/0251265 A1 * | 12/2004 | FitzSimons et al. ............ 221/92 |
| 2007/0157877 A1 | 7/2007 | Barnes, III |
| 2007/0181594 A1 | 8/2007 | Thompson |
| 2007/0290094 A1 * | 12/2007 | Anderson ............ 242/594 |
| 2008/0164277 A1 | 7/2008 | Platt |
| 2009/0032553 A1 * | 2/2009 | Eddy ............ 222/192 |
| 2009/0184010 A1 * | 7/2009 | Palamountain ............ 206/226 |
| 2010/0068092 A1 * | 3/2010 | Larsson ............ 422/5 |
| 2011/0315715 A1 | 12/2011 | Ophardt |

\* cited by examiner

COMBINATION TOILET PAPER DISPENSER, DISINFECTING STATION, AND DEODORIZING STATION

This application claims the benefit of U.S. Provisional Patent Application No. 61/471,235 filed Apr. 4, 2011.

FIELD OF THE INVENTION

The present invention relates generally to the field of restroom fixtures, and, more particularly, to a fixture that dispenses toilet paper, disinfectant wipes, and a deodorizing fragrance.

BACKGROUND OF THE INVENTION

There remains a long-felt need for a simple and convenient system to provide dry toilet paper in a bathroom and also provide a wet wipe for cleaning and disinfecting surfaces in the bathroom. There is also a long-felt need for a simple and convenient system to provide toilet paper and also provide a deodorizing fragrance in the bathroom.

As shown and described in U.S. Pat. No. 5,887,759 to Ayigbe, there have been a variety of prior art devices used for moistening toilet paper and the like. Such devices have generally employed the use of water from the toilet tank and in so doing it has been difficult to control the wetness. By being unable to control the wetness, the tissue strength has been weakened to where the tissue may disintegrate. Other devices have consisted of separate supply systems for moistening toilet tissue, but these have been bulky, relatively inefficient, and expensive. In addition, some devices have generally only been used for moistening the tissue separate and apart from the roll of tissue and not usable in conjunction with a roll of toilet tissue which can be mounted with respect to the dispenser and thus make for a simple compact unit that surrounds the roll and thus require very little space.

In the '759 patent, Ayigbe suggested a dispenser for moistening paper articles consisting of an H-shaped structure in which the central section and the end sections together serve as a reservoir for a liquid such as a disinfectant or moisturizer. The dispenser fits over a roll of toilet tissue and the central section includes a spray pump for directing a fine mist spray onto sheets of toilet tissue. If desired, the roll support can be a unitary part of the dispenser assembly.

This and other proposed solutions to this problem have obvious drawbacks. A soft, non-abrasive toilet paper is simply not designed and manufactured to serve as a wet-wipe to clean and disinfect surfaces of the bathroom. On the other hand, a wipe that is suitable for cleaning and disinfecting surfaces is not suitable as a toilet paper. Further, none of the proposed solutions include a means of dispensing a deodorant into the bathroom to clear bathroom odors.

The present invention is directed to solving these and other drawbacks in the art.

SUMMARY OF THE INVENTION

The present invention includes a standard commercial or other double roll toilet paper dispenser made from a plastic type material. The paper dispenser, together with the other structural features described herein, is referred to as a station. The station further includes a cover which houses a fan that pulls air from inside the dispenser. Inside the base of the station, centered at the top, is a tray that holds a fragrance cup holding a quantity of deodorant. The fragrance and fan together create a deodorizing feature for the station housed in a commercial toilet paper dispenser energized by a battery power source.

The base holds two rolls of commercial toilet paper that roll on a plastic axle. The axle is hollowed out and one axle stores a bottle that dispenses a hand sanitizing towel. The other axle stores a bottle that dispenses a surface disinfecting towel.

A microswitch may be integrated in the cover that will disengage the fan when the cover of the unit is open.

These and other features and advantages of this invention will be readily apparent to those skilled in the art.

BRIEF DESCRIPTION OF THE DRAWINGS

So that the manner in which the above recited features, advantages and objects of the present invention are attained and can be understood in detail, more particular description of the invention, briefly summarized above, may be had by reference to embodiments thereof which are illustrated in the appended drawings.

DETAILED DESCRIPTION OF PREFERRED EMBODIMENTS

Figure 1:
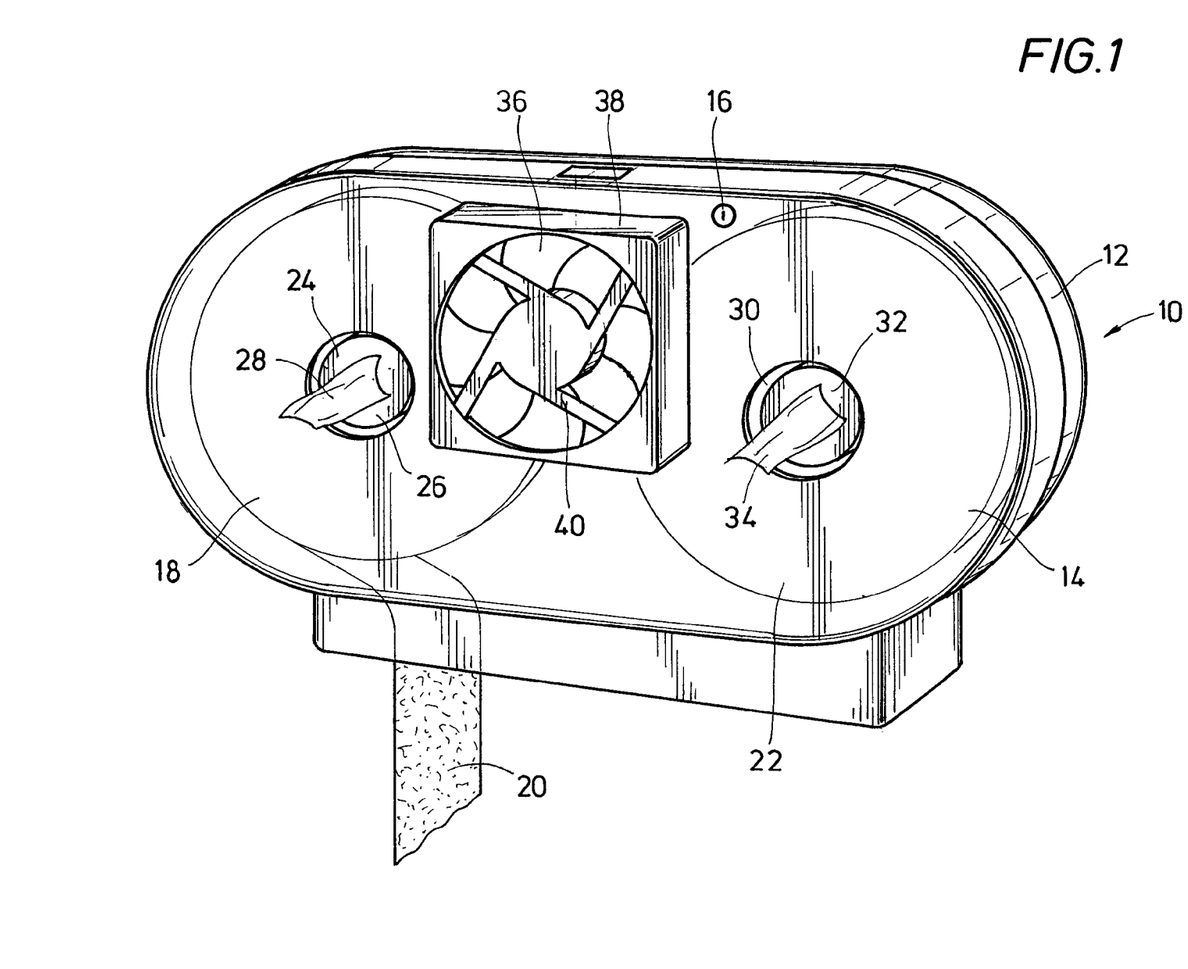
FIG. 1 is a perspective view of a combination station in accordance with the teachings of this invention.

FIG. 1 depicts a presently preferred embodiment of a station 10 of the present invention. A mount body 12 is secured to a wall or partition 72 (See FIGS. 3 and 4) in the conventional manner. A front cover 14 secures to the mount body 12 to form an enclosure. A conventional lock 16 may hold the front cover 14 to the mount body to deter tampering. However, FIGS. 8-11 illustrate a presently preferred key and latch arrangement to more effectively deter such tampering.

The enclosure, comprising the mount body 12 and the front cover 14, retains a roll of toilet paper 18 which is accessible to the user as a paper end 20. Preferably, a second roll 22 is placed within the enclosure for ease of access by the user.

Figure 5:
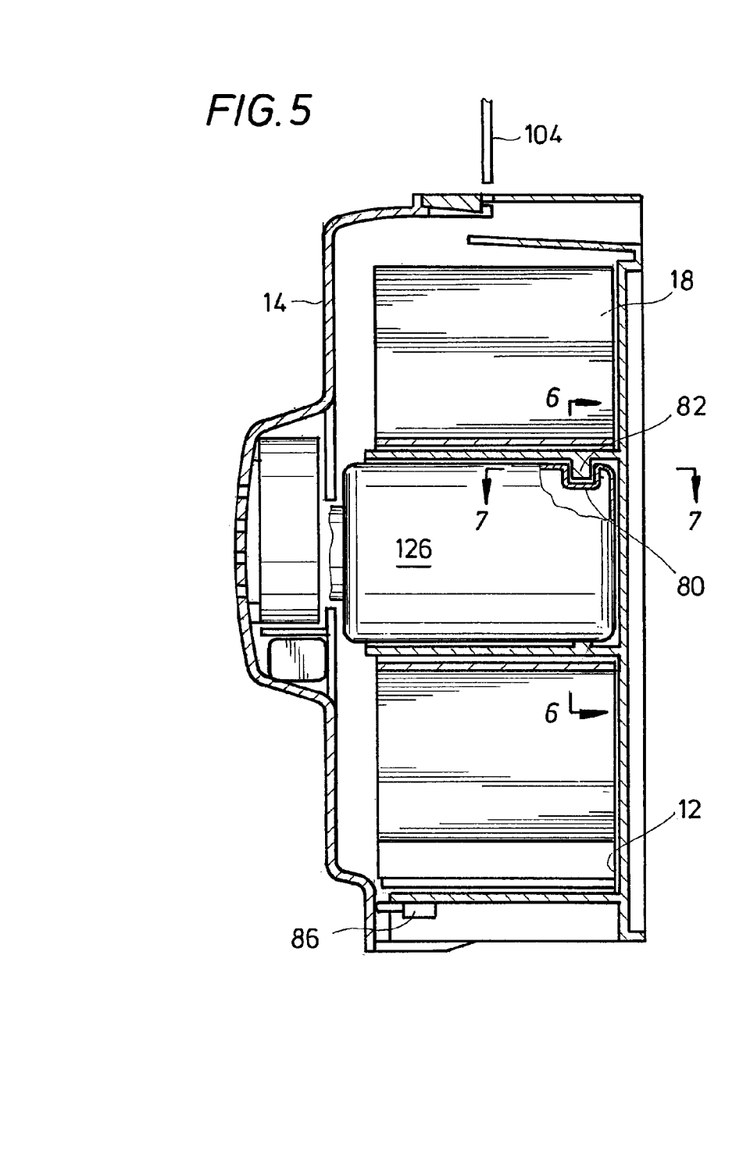
FIG. 5 is a side section of another preferred embodiment of the station illustrating placement of a dispensing bottle.
Figure 6:
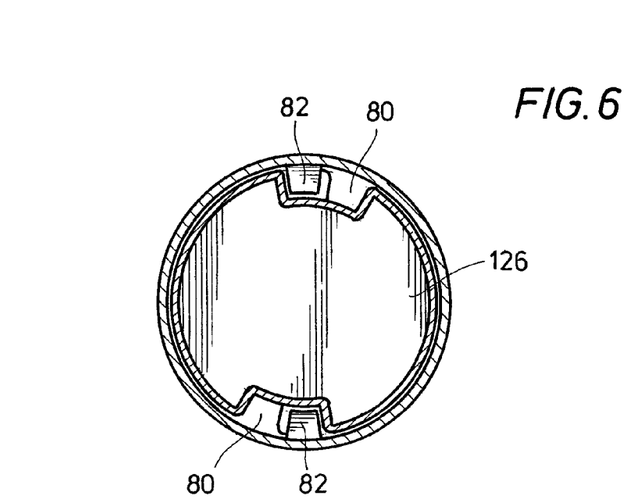
FIG. 6 is a section view of a dispensing bottle and its holder as taken along section lines 6-6 of FIG. 5.
Figure 7:
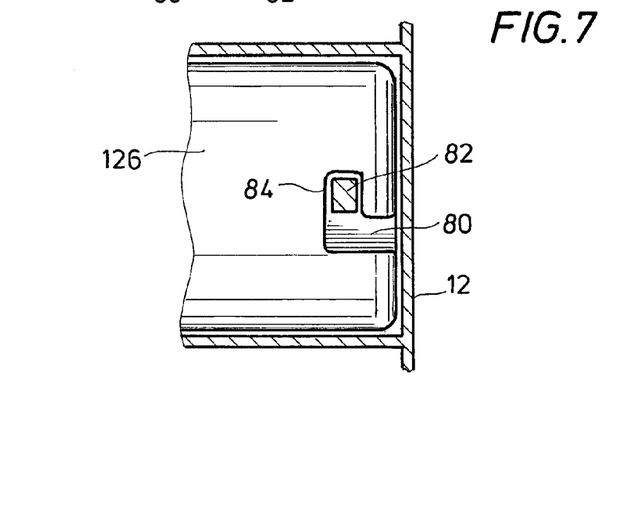
FIG. 7 is a detail section view of a bottle mount feature as taken along section lines 7-7 of FIG. 5.

The roll 18 turns on an axle 24. The axle 24 is hollow, to permit mounting a bottle 26 which retains a quantity of disinfectant wipes 28. This way, a wipe 28 may be pulled from the bottle 26 and used to wipe down a soiled surface within the area in vicinity of the station 10. Similarly, the second roll 22 turns on a hollow axle 30 with a bottle 32 within the hollow axle 30 arranged to dispense a hand-cleansing wipe 34. In the embodiment illustrated in FIG. 2, a plurality of gripping fingers 33 are provided within a housing 35 is securely yet removably hold the bottle 26. Similar gripping fingers 37 are provided in a housing 39 to retain the bottle 32. FIGS. 5-7 depict a presently preferred embodiment of an arrangement for securing the bottles 26 and 32.

Those of skill in the art will appreciate that that a single roll may be used, and either a single bottle of wipes employed or a pair of opposing hemi-cylindrical bottles with hand wipes and surface wipes provided. Also, paper towels for drying ones hands may be used, rather than toilet paper, or one or each may be used within the scope and spirit of this invention.

Figure 2:
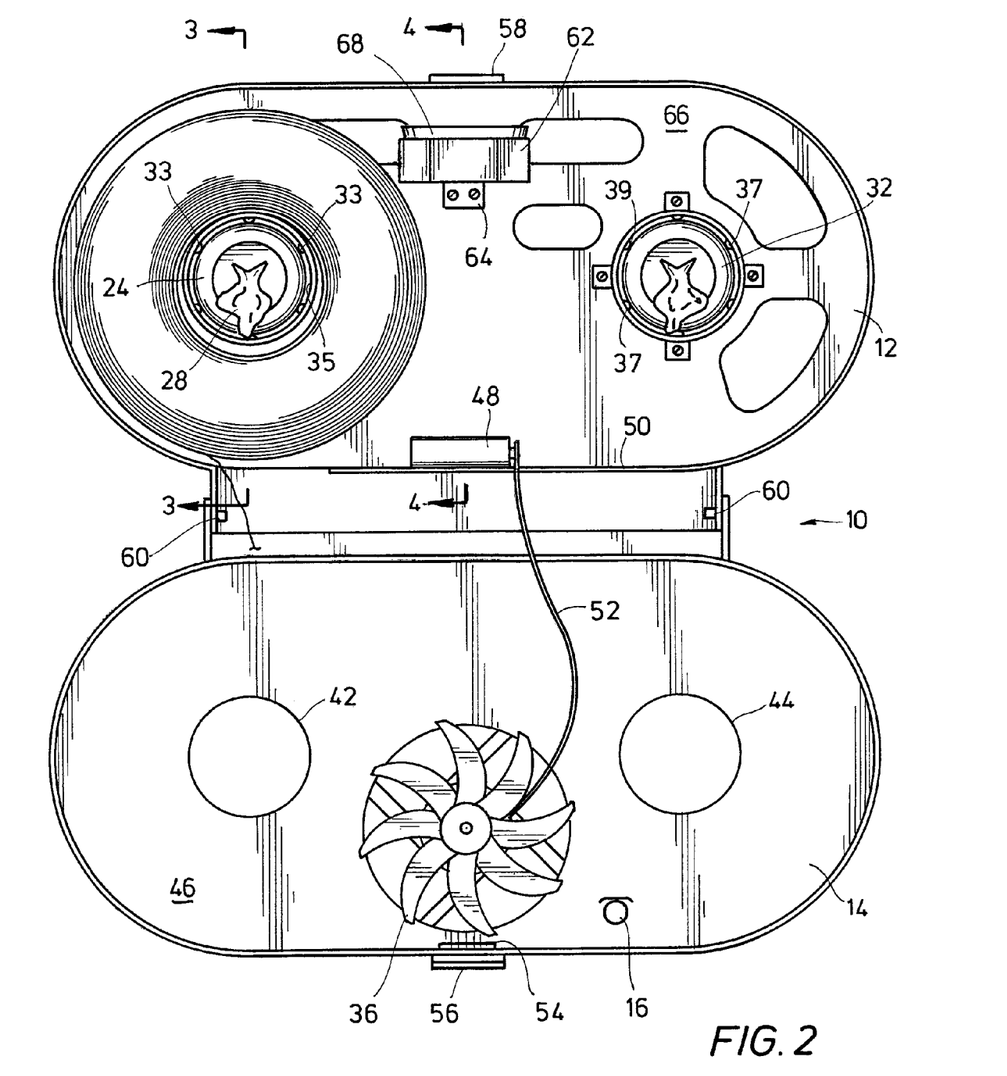
FIG. 2 is front view of the station with the front door open.

A fan 36 is mounted within a housing 38 and is preferably covered by a grill 40 with ventilation openings to provide for the transfer of scented air as well as to keep fingers or other items out of the fan. The fan may be battery powered, as shown in FIG. 2, or may be hard-wired to an electrical power source. Preferably, the fan draws air from within the enclosure and blows out scented air into the environment of the station, as described below.

FIG. 2 illustrates a presently preferred arrangement of the inside of the station 10. As previously described, the mount body 12 is secured to the wall or partition 72 and the front cover 14 secures to the mount body 12 to form an enclosure. In the embodiment of FIGS. 1 and 2, the lock 16 holds the front cover 14 to the mount body to deter tampering. A presently preferred embodiment of a latch and key arrangement is shown and described below in respect of FIGS. 8-11.

As shown in FIG. 2, a hole 42 is formed in the front cover 14 to allow access to the disinfectant wipes 28 by a user. Similarly, a hole 44 is formed in the front cover 14 to allow access to the hand-cleansing wipes 34 by the user. Preferably, the diameter of the hole 42 is smaller than the diameter of the bottle 24 and the diameter of the hole 44 is smaller than the diameter of the bottle 32 so that a user is forced to withdraw only one wipe 28 or 34 at a time. Also, in this way, the front cover must be opened in order to withdraw the bottle 24 or 32 and to replace it with a fresh supply of wipes.

FIG. 2 also shows the positioning of the fan 36 inside a back surface 46 of the front cover 14. A battery 48 is preferably mounted on a base 50 formed in the bottom of the mount body 12. A wire 52 carries DC electrical power to the fan 36. If desired, a microswitch 54 may be mounted in association with the fan so that electrical power is interrupted when the front cover 14 is opened. The microswitch 54 may also be associated with a latch 56 which mates with a detent 58 at the top of the mount body 12. Also, the front cover 14 is preferably mounted to mount body 12 by way of a hinge 60. As previously mentioned, the key and latch arrangement illustrated in FIGS. 8-11 is the presently preferred embodiment.

A cup 62 is preferably mounted with a mount 64 to a back wall 66 of the mount body. The cup 62 is conveniently arranged to retain a container 68 of a deodorant, such as a gel. Note that when the front cover 14 is shut, the fan is immediately adjacent the container 68 of the deodorant so that, as the fan turns, it draws scented air out of the enclosure formed by the mount body and the front cover, and blows the scented air out into the room in which the present invention is positioned, thereby reducing unpleasant odors. Conventionally, one single deodorant station is mounted within a public bathroom, and mounted high on a wall to reduce tampering. By including the deodorant station within the enclosure as just described, a deodorant is provided for each toilet paper and wipe dispensing combination, making the deodorizing feature far more effective.

Figure 3:
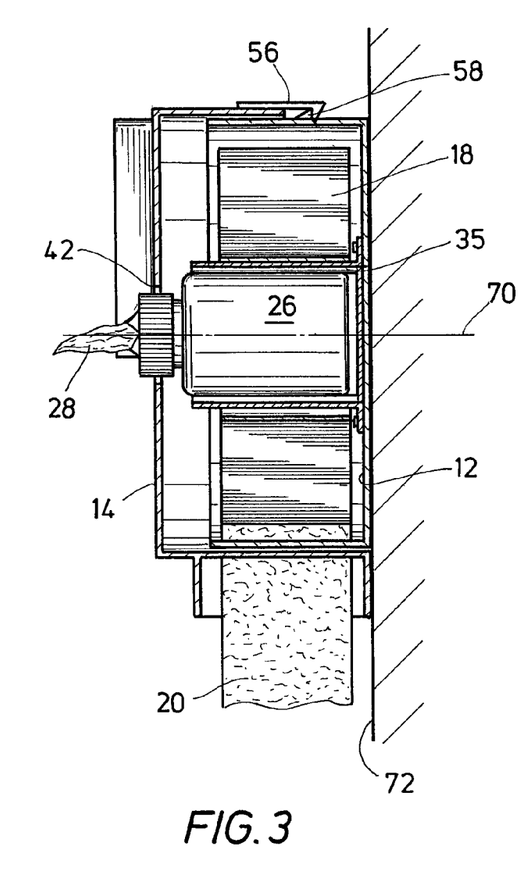
FIG. 3 is a side section view taken along section lines 3-3 in FIG. 2 (but with the cover shut).

FIG. 3 shows a side section view of the invention taken through the toilet paper roll 18 and the bottle 26, assuming that the cover is shut. Those of skill in the art will recognize that a similar arrangement is preferably provided in respect of the bottle 34. The bottle 26 and the toilet paper roll 18 are coaxially arranged about an axis 70. In the embodiment of FIG. 3, the bottle is grasped within the housing 35. A presently preferred embodiment for retaining the bottles is depicted in FIGS. 5-7. The housing 35 is mounted to the mount body 12, which in turn is secured to the wall or partition 72. Note that the hole 42, through which a wipe 28 may be accessed, is smaller than the diameter of the bottle 26 so that the front cover 14 must be opened before the bottle can be changed out. Also note that the latch 56 and detent cooperate to hold the front cover firmly closed.

Figure 4:
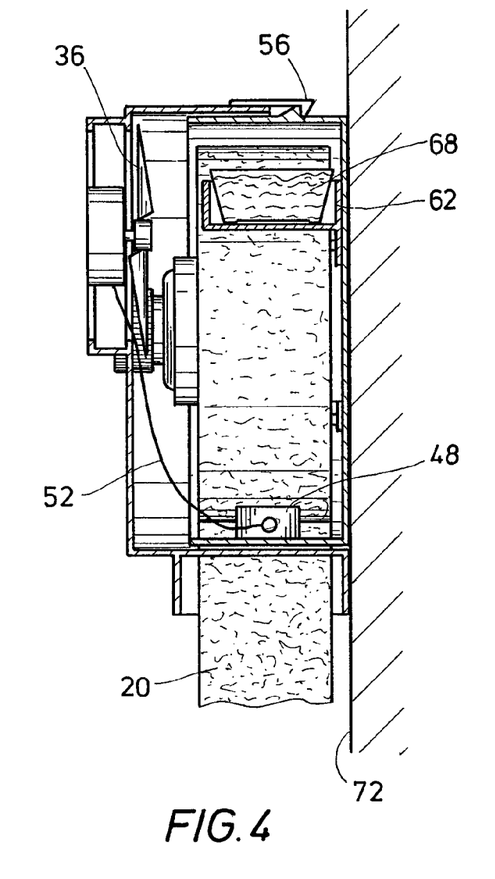
FIG. 4 is a side section view taken along section lines 4-4 in FIG. 2 (but with the cover shut).

FIG. 4 shows a side section view of the invention through the deodorant station, the fan, and the battery, assuming that the cover is shut. The cup 62 is arranged to retain the container 68 of a deodorant immediately adjacent the fan 36 so that the fan draws scented air from the enclosure out into the room in which the station is mounted.

FIGS. 5-7 illustrated a presently preferred embodiment of a structure to retain a bottle 126 within the enclosure. The bottle 126 includes an "L" shaped recess 80 arranged to mate with a registration tab 82. As shown in FIG. 6, a pair of recesses 80 may be provided, along with a complementary registration tabs 82, with which to mate. Alternatively, a single recess and tab may be included. In operation, the bottle is inserted so that the portion of the recess parallel to the axis of the bottle slides over the registration tab. Then, when the bottle bottoms out, the bottle is rotated by a few degrees until the tab is positioned in a "toe" 84 of the recess. To remove the bottle, the procedure is reversed and a new bottle of wipes is inserted.

Note also in FIG. 5 that a plunger type microswitch 86 is shown. With the cover 14 is opened, the plunger of the microswitch 86 is released and the electrical circuit providing power of the motor of the fan 36 is interrupted. The plunger is depressed when the cover 14 is shut, completing the electrical circuit.

Finally, FIGS. 8-11 illustrate a presently preferred novel key and latch arrangement. The mount body 12 and the cover 14 are as previously described. The cover 14 preferably includes a male portion 90 of a latch and the mount body 12 may include a female portion 92 of the latch, although these elements may be reversed.

Figures 9, 10:
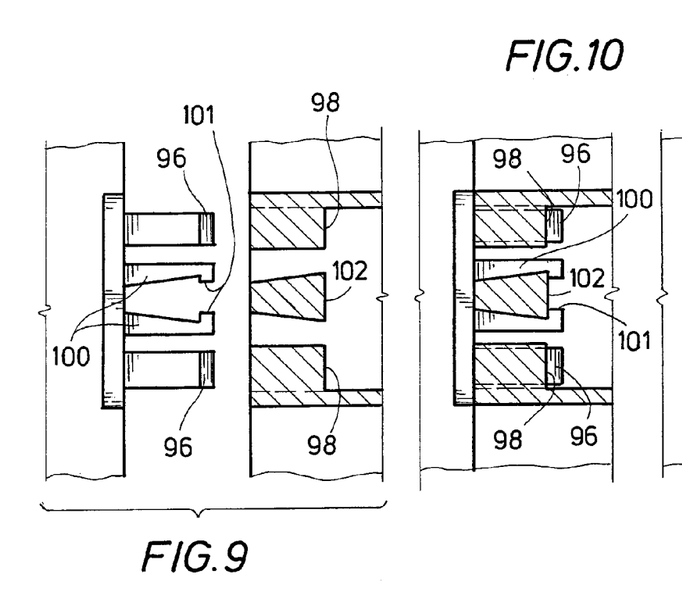
FIG. 9 is a section view of the latch of FIG. 9, as seen along section lines 9-9 with the key detached from the latch.
FIG. 10 is a section view of the latch of FIG. 9 with the key inserted into the latch just to the point of contact with the latch.

The male portion 90 of the latch includes an outer pair of fingers 94. The fingers 94 include upwardly pending tabs 96 arranged to grasp a pair of ledges 98 (FIG. 9). The male portion 90 also includes an inner pair of fingers 100 including inwardly depending tabs 101 arranged to grasp a trapezoidal post 102. As the cover 14 is closed, the male portion 90 is inserted into the female portion 92, the outer pair of fingers 94 bend down until the tabs 96 extend beyond the ledges 98, and the inner pair of fingers 100 are forced apart until the tabs 101 extend beyond the post 102. The latch is therefore dual-acting, and no standard jimmying tool will work to open the latch.

Figure 8:
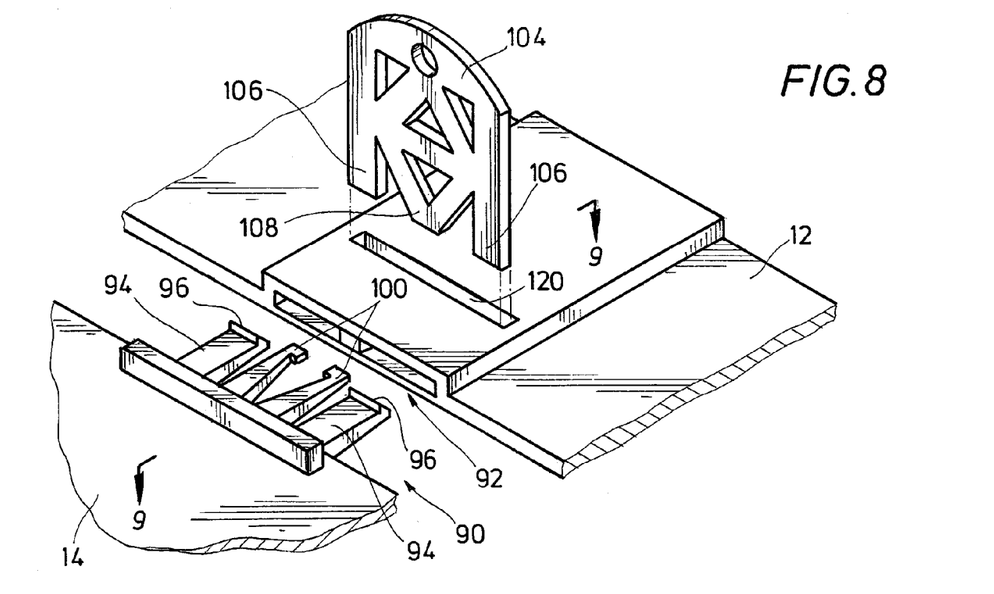
FIG. 8 is a perspective view in partial section of a key and latch feature of the station.
Figure 11:
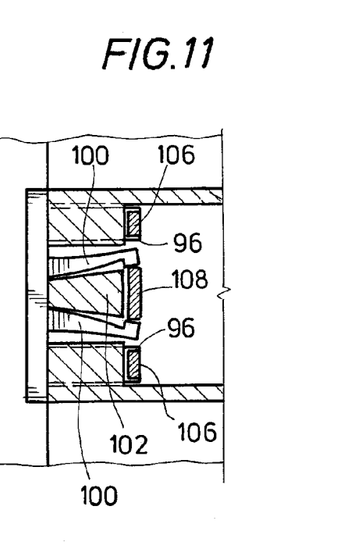
FIG. 11 is a section view of the latch of FIG. 9 with the key opening the latch.

To open the latch requires a key 104 shown in FIGS. 8 and 11. The key 104 includes a pair of outer prongs 106 and a middle prong. The outer prongs 106 are sized and oriented to press down on the tabs 96 when the key 104 is inserted into a slot 120 until they disengage the ledges 98. Also, the middle prong 108 is sized and oriented to slide between the tabs 101, forcing them apart until the tabs clear the post 102. With the key staying with the slot 120, the latch can then be disengaged and the cover 14 opened.

The principles, preferred embodiments, and modes of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A station comprising:
   a paper dispenser having a hollow axle;
   a wet wipe dispenser removably positioned within the hollow axle of the paper dispenser;
   a source of a deodorizing scent;
   a cover that opens and closes, wherein the cover is secured to a mount body to form an enclosure that contains the paper dispenser, the wet wipe dispenser, and the source of the deodorizing scent, and wherein a hole is formed in the cover to allow access to a wet wipe in the wet wipe dispenser; and
   a fan mounted within a housing on the cover, wherein when the cover is closed the fan is adjacent the source of the deodorizing scent and positioned to pull scented air from inside the enclosure and blow the scented air out of the enclosure.

2. The station of claim 1, wherein the paper dispenser is a toilet paper dispenser.

3. The station of claim 1, wherein the wet wipe dispenser is a dispenser of hand sanitizing towels.

4. The station of claim 1, further comprising a latch between the cover and the mount body.

5. The station of claim 1, wherein the source of the deodorizing scent comprises a cup mounted with a mount to the mount body, and wherein the cup retains a container of a quantity of deodorant.

6. The station of claim 1, wherein the wet wipe dispenser is a dispenser of hand sanitizing towels, surface wipes, or both.

7. The station of claim 1, further comprising a battery and connecting circuitry to power the fan.

8. The station of claim 7, further comprising a microswitch in the connecting circuitry to control electrical power of the fan.

9. The station of claim 1, wherein the wet wipe dispenser comprises a bottle that is removably positioned within the hollow axle.

10. A station comprising:
    a paper dispenser;
    a wet wipe dispenser;
    a source of a deodorizing scent;
    an enclosure containing the paper dispenser, the wet wipe dispenser, and the source of the deodorizing scent wherein the enclosure comprises a cover and a mount body; and
    a fan mounted within a housing on the cover, wherein when the cover is closed the fan is adjacent the source of the deodorizing scent and positioned to pull scented air from inside the enclosure and blow the scented air out of the enclosure;
    wherein the paper dispenser includes a hollow axle and further wherein the wet wipe dispenser comprises a bottle that is removably positioned within the hollow axle, and wherein the bottle includes an "L" shaped recess and the hollow axle includes an inwardly depending tab to engage the "L" shaped recess of the bottle.

11. A station comprising:
    a cover that opens and closes, wherein the cover is secured to a mount body to form an enclosure;
    a first toilet paper dispenser defining a first hollow axle joined to the mount body;
    a second toilet paper dispenser defining a second hollow axle joined to the mount body;
    a wet hand-wipe dispenser removably positioned within the first hollow axle, and a first hole formed in the cover to allow access to a wet hand sanitizing towel in the wet hand-wipe dispenser;
    a wet surface wipe dispenser removably positioned within the second hollow axle, and a second hole formed in the cover to allow access to a wet surface wipe in the wet surface wipe dispenser;
    a source of a deodorizing scent within the enclosure, wherein the enclosure contains the first toilet paper dispenser, the second toilet paper dispenser, the wet hand-wipe dispenser, the wet surface wipe dispenser, and the source of the deodorizing scent; and
    a fan mounted within a housing on the cover, wherein when the cover is closed the fan is adjacent the source of the deodorizing scent and positioned to pull scented air from inside the enclosure and blow the scented air out of the enclosure.

12. The station of claim 11, further comprising:
    a battery and connecting circuitry to power the fan; and
    a microswitch in the connecting circuitry to control electrical power to the fan.

13. The station of claim 11, further comprising a key and wherein the latch includes a male portion and a female portion, and further wherein the male portion comprises:
    a. a pair of outer fingers, each of the outer fingers including an upwardly depending tab; and
    b. a pair of inner fingers, each of the inner fingers including an inwardly depending tab; and further wherein the key comprises:
    c. a pair of outer prongs arranged to abuttingly contact the upwardly depending tabs of the outer fingers; and
    d. an inner prong arranged to force apart the inner fingers by engaging the inner fingers.

14. The station of claim 11, wherein the source of the deodorizing scent comprises a container of a quantity of deodorant that is a gel.

15. The station of claim 14, wherein the source of the deodorizing scent comprises a cup mounted with a mount to the mount body that holds the container of the quantity of deodorant.

16. A station comprising:
    a paper dispenser;
    a wipe dispenser;
    a source of a deodorizing scent;
    an enclosure containing the paper dispenser, the wipe dispenser, and the source of the deodorizing scent, wherein the enclosure comprises a cover, a mount body, and a latch between the cover and the mount body; and
    a key, wherein the latch includes a male portion and a female portion, and further wherein the male portion comprises:
    a. a pair of outer fingers, each of the outer fingers including an upwardly depending tab; and
    b. a pair of inner fingers, each of the inner fingers including an inwardly depending tab; and further wherein the key comprises:
    c. a pair of outer prongs arranged to abuttingly contact the upwardly depending tabs of the outer fingers; and
    d. an inner prong arranged to force apart the inner fingers by engaging the inner fingers.

17. A station comprising:
    a paper dispenser that includes a hollow axle;
    a wet wipe dispenser removably positioned within the hollow axle;
    a cover that opens and closes, wherein the cover is secured to a mount body to form an enclosure containing the paper dispenser and the wet wipe dispenser, wherein a hole is formed in the cover to allow access to a wet wipe in the wet wipe dispenser; and a fan, wherein when the cover is closed the fan is positioned adjacent a source of a deodorizing scent to pull scented air from inside the enclosure and blow the scented air out of the enclosure.

18. The station of claim 17, wherein the wet wipe dispenser comprises a bottle, and wherein a diameter of the hole formed in the cover is smaller than a diameter of the bottle.

19. The station of claim 17, wherein the wet wipe dispenser comprises a bottle, and wherein the bottle includes an "L" shaped recess and the hollow axle includes an inwardly depending tab to engage the "L" shaped recess of the bottle.

20. The station of claim 17, wherein the wet wipe dispenser comprises a bottle, and wherein the bottle is grasped in a housing and removably positioned within the hollow axle, and wherein the housing is mounted to the mount body.

\* \* \* \* \*